(12) United States Patent
Davis-Turak et al.

(10) Patent No.: US 11,387,003 B2
(45) Date of Patent: Jul. 12, 2022

(54) METHOD FOR SYSTEMS OF NOTEBOOKS OF GENOMIC DATA NETWORKS

(71) Applicant: ROSALIND, INC., San Diego, CA (US)

(72) Inventors: Jeremy Davis-Turak, San Diego, CA (US); Roshni Patel, San Diego, CA (US); Aaron Stanz, San Diego, CA (US); Jean Lozach, San Diego, CA (US); James Belemonti, San Diego, CA (US); Gabriel Giestas, San Diego, CA (US); Cassandra Wesselman, San Diego, CA (US); Timothy Wesselman, San Diego, CA (US)

(73) Assignee: ROSALIND, INC., San Diego, CA (US)

( * ) Notice: Subject to any disclaimer, the term of this patent is extended or adjusted under 35 U.S.C. 154(b) by 0 days.

(21) Appl. No.: 17/207,140

(22) Filed: Mar. 19, 2021

(65) Prior Publication Data

US 2021/0210215 A1 Jul. 8, 2021

Related U.S. Application Data

(63) Continuation-in-part of application No. 16/432,294, filed on Jun. 5, 2019, now abandoned, which is a continuation-in-part of application No. 15/715,712, filed on Sep. 26, 2017, now Pat. No. 10,331,848.

(60) Provisional application No. 62/452,894, filed on Jan. 31, 2017, provisional application No. 62/452,888, filed on Jan. 31, 2017.

(51) Int. Cl.
*G06F 16/33* (2019.01)
*G16H 50/70* (2018.01)
*G06F 21/62* (2013.01)
*G06F 16/25* (2019.01)
*G06F 16/9538* (2019.01)

(52) U.S. Cl.
CPC ............ *G16H 50/70* (2018.01); *G06F 16/258* (2019.01); *G06F 16/9538* (2019.01); *G06F 21/6245* (2013.01)

(58) Field of Classification Search
CPC ..... G06F 16/33; G06F 16/338; G06F 16/3344
See application file for complete search history.

(56) References Cited

U.S. PATENT DOCUMENTS

2004/0260717 A1* 12/2004 Albornoz .............. G06F 16/954
707/999.102

* cited by examiner

*Primary Examiner* — Grace Park
(74) *Attorney, Agent, or Firm* — Nguyen Tarbet LLC (57) ABSTRACT

The present invention is directed to systems and methods for displaying and contributing to a database of genomic information in a notebook-like format, with emphasis on establishing and viewing relationships between data points in the database. The present invention features a server containing the database of genomic information and a computing device communicatively coupled to the database. The computing device may comprise a Note Input Module for allowing the user to input a note into the database of genomic information. The note may be associated with a first data point and connect it to one or more second data points. The computing device may further comprise a Note Association Module for adding to the list of associated data points of a pre-existing note. The computing device may further comprise a Browsing Module for allowing a user to search the database of genomic information for data points and notes.

12 Claims, 11 Drawing Sheets

METHOD FOR SYSTEMS OF NOTEBOOKS OF GENOMIC DATA NETWORKS

CROSS-REFERENCES TO RELATED APPLICATIONS

This application is a continuation-in-part and claims benefit of U.S. patent application Ser. No. 16/432,294 filed Jun. 5, 2019, which is a continuation-in-part of U.S. Non-Provisional application Ser. No. 15/715,712 filed Sep. 26, 2017, now U.S. Pat. No. 10,331,848, which claims benefit to U.S. Provisional Patent Application No. 62/452,888, filed on Jan. 31, 2017, and U.S. Provisional Patent Application No. 62/452,894, filed on Jan. 31, 2017, the specification(s) of which are incorporated herein in their entirety by reference.

FIELD OF THE INVENTION

The present invention is directed to systems and methods for displaying and contributing to a database of genomic information in a notebook-like format, with emphasis on establishing and viewing relationships between data points in the database.

BACKGROUND OF THE INVENTION

The field of genomics has a vast wealth of data points that affect other data points in various ways. Some databases containing these genomic data points have been refined to collections of derivative data and metadata, and scientists must sift and sort through these records to glean insights. These insights use a variety of personal knowledge, institutional knowledge and public resources, either in the form of published papers or structured public databases. As users review and interpret complex genomic (transcriptomic, proteomic, etc.) results, they have the need to capture notes, representing relationships and connections identified in the data. Thus, there exists a present need for a system that allows scientists to sort, view, and contribute insights to a large database of genomic information as well as view and establish relationships between data points of the database of genomic information.

BRIEF SUMMARY OF THE INVENTION

It is an objective of the present invention to provide systems and methods that allow for displaying and contributing to a database of genomic information in a notebook-like format, with emphasis on establishing and viewing relationships between data points in the database, as specified in the independent claims. Embodiments of the invention are given in the dependent claims. Embodiments of the present invention can be freely combined with each other if they are not mutually exclusive.

The present invention features a system for allowing a user to access and contribute to a database of genomic information. In some embodiments, the system may comprise a server containing the database of genomic information, comprising a collection of derivative genomic data and a collection of metadata relating to the collection of the derivative genomic data. The system may further comprise a computing device communicatively coupled to the database of genomic information. The computing device may comprise a Note Input Module for allowing the user to input a note into the database of genomic information. The note may be associated with a first data point and connect it to one or more second data points of the database of genomic information. The Note Input Module may accept the note as input from the user and associate it with the first data point. The Note Input Module may identify, from the note, one or more data points to be associated with the first data point, thus establishing a relationship between the first data point and the one or more data points. The computing device may further comprise a Note Association Module for adding to the list of associated data points of a pre-existing note.

The computing device may further comprise a Browsing Module for allowing a user to search the database of genomic information for data points and notes. In some embodiments, the Browsing Module may comprise instructions for displaying a full set of data points of the database of genomic information. The Browsing Module may accept a search term from the user and a search category. If the search category is data points, the Browsing Module may retrieve one or more data points from the database, and if the search category is notes, the Browsing Module may retrieve one or more notes from the database. The Browsing Module may display the data points or notes and allow the user to select a data point or note and view additional data. The computing device may further comprise a Scoring Module for assigning a score to a data point or a note. In some embodiments, the Scoring Module may comprise instructions for calculating the score for the data point or the note, assigning the score to the data point or the note, and displaying the score of the data point or the note. The score of a data point may be calculated based on a number of supporting data points associated with the data point.

One of the unique and inventive technical features of the present invention is the capability of a user to contribute to the database of genomic information by linking data points to each other with a note for other users to view. Without wishing to limit the invention to any theory or mechanism, it is believed that the technical feature of the present invention advantageously provides for a notebook-style database of a massive quantity of user insights that can be contributed to by a massive quantity of users. None of the presently known prior references or work has the unique inventive technical feature of the present invention.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which.

DETAILED DESCRIPTION OF THE INVENTION

Figure 6A:
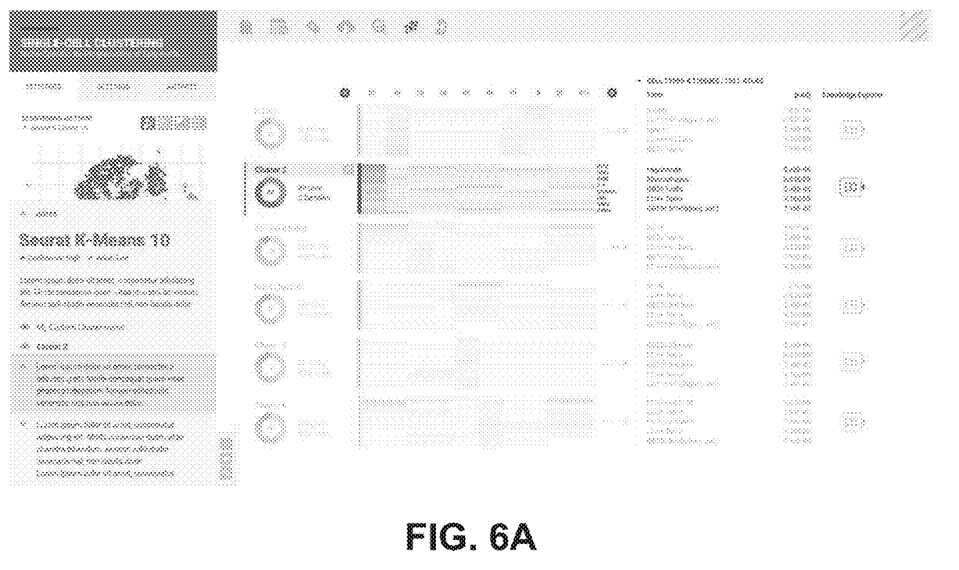
FIG. 6A shows a screenshot of an interface of an embodiment of the present invention showing expanded data and a plurality of notes associated with a selected data point.
Figure 6B:
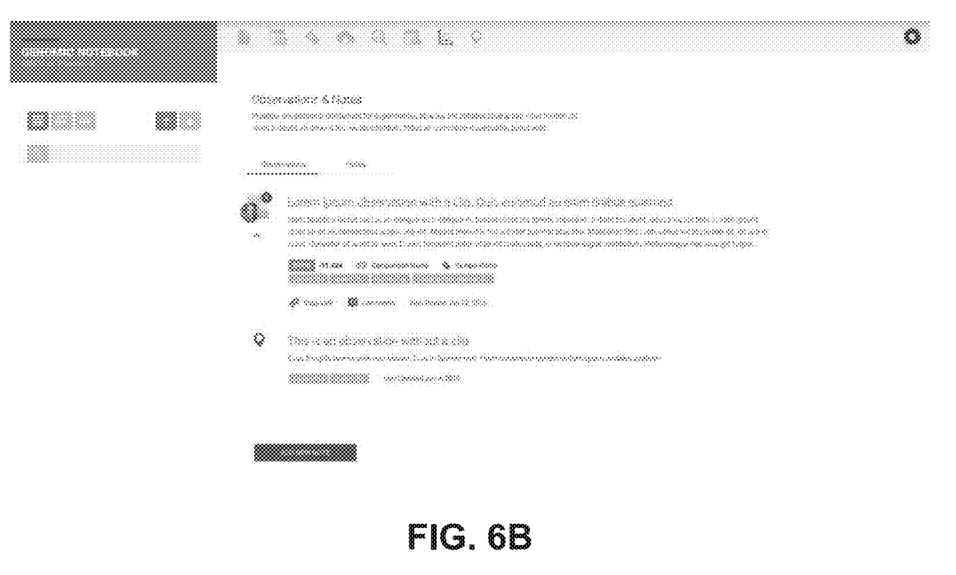
FIG. 6B shows a screenshot of an interface of an embodiment of the present invention showing a set of notes as well as the ability to add a new note.

Following is a list of elements corresponding to a particular element referred to herein:
100 system
200 server
210 database of genomic information
300 computing device
310 Note Input Module
320 Note Association Module
330 Browsing Module
340 Scoring Module
400 user
500 note
505 first data point
510 pre-existing note
515 new second data points
520 search term
522 search category
525 retrieved data points
527 retrieved notes
530 score
535 user score The interface of the present invention allows the user to select a data point and add a Note (see FIGS. 6A-6B). The interface stores the data point, including its name, values, direction, significance, list membership, the surrounding context of the data point, any data input by the user as well as the session state and any other relationships related to the data point. Some of these include the existence of prior Notes on the same data point from any user on the system. User permissions dictate what is visible, while the existence of any Note and relationship is weighted in importance by rank and correlation, improving the value of the Note (insight). This would likely take the form of a special score that pulls from the unified knowledge to help guide every scientist while protecting the confidentiality of every data point that contributes to the ranking/confidence scoring for the Note.

Note may also include a series of comments, which may or may not be threaded to a particular comment or text, by any number of users who have access to the data and Notes as may be represented in various forms, including but not limited to the notebook view, the interactive analysis of data results exploration or other genomic data visualizations. The present invention seeks to extend the metadata foundation of existing genomic databases to new graph-based notebooks of user insights that enable unified knowledge. Notes also contain a series of sub-notes, referred to as Observations, that are encapsulated within the Note. All Notes are encapsulated into a binder (Graph-based Notebook) that can be cross referenced throughout the system via notes, search, and the formation of presentations. The evolution of an Observation may be as follows: Observations→Weighted Observation→Formalized Notes→Reports/Presentations.

Figure 6C:
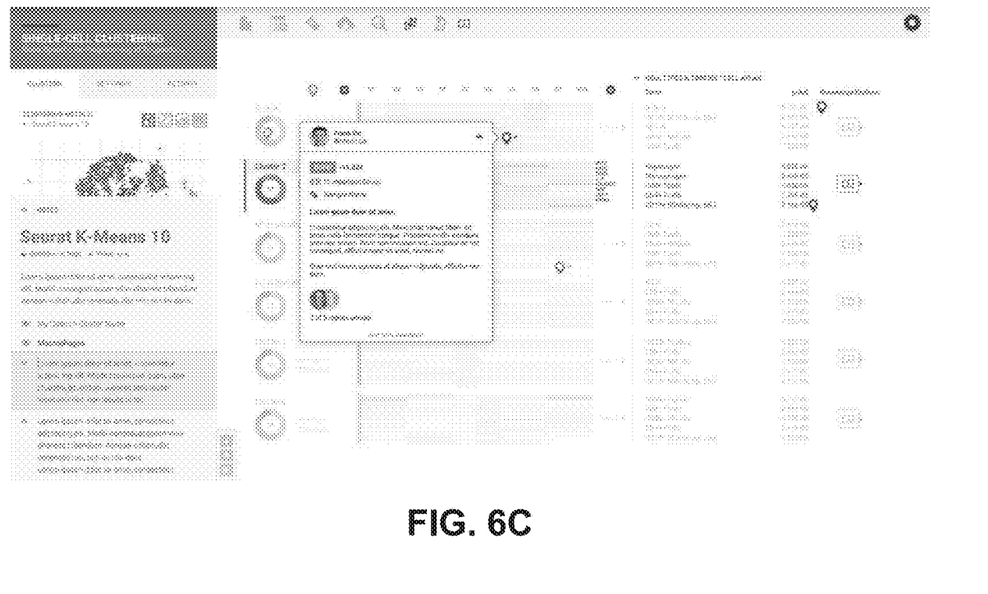
FIG. 6C shows a screenshot of an interface of an embodiment of the present invention showing a link between a selected data point and a related data point.
Figure 6D:
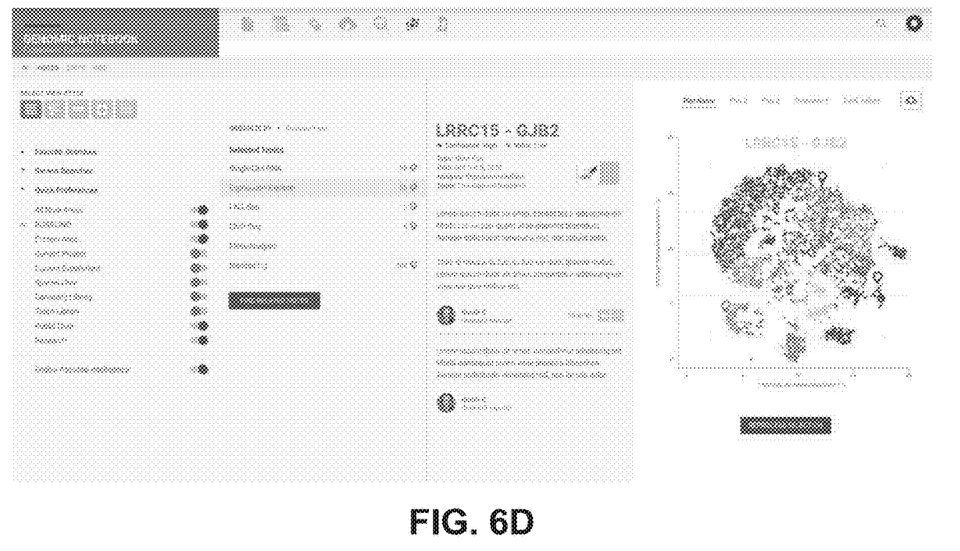
FIG. 6D shows a screenshot of an interface of an embodiment of the present invention showing a method of the Browsing Module for displaying the data in both a notebook view (left) and a knowledge graph view (right).
Figure 6E:
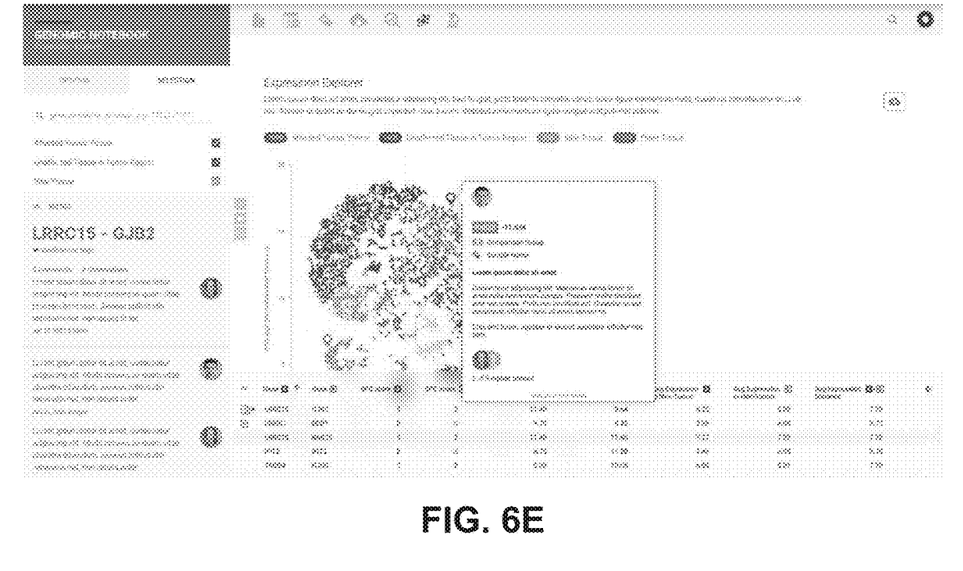
FIG. 6E shows a screenshot of an interface of an embodiment of the present invention showing a knowledge graph of data points.

As a graph-based notebook, every Note (observation) stores relationships and is viewable and searchable in any context—including the traditional (and less efficient) means by chronology (see FIG. 6D), or structure (chapter, subject, project) AND much more interestingly, by the relationships that bind the insights. Notes and Observations by the gene or genomic object that defines/underlies the insight and its relationships to all else. Imagine having a notebook that could show all your Notes and their relationships on any gene, pathway, disease or drug. In collaboration, this extends the concept of a "lab notebook" as a collective, mineable, searchable collection of research and insights that ultimately empower scientists to share, explore, rank, respond, comment and discover patterns, functions and relationships that unlock the secrets of biology.

Within the interface (see FIG. 6A), a simplified view focuses on the user input and shows the containing object and any other Notes on the same data point, including Notes from other authors (as is permissible). In this Simplified view, the System stores metadata, relationships, data values and links to other visualizations of the data (eg, a bar plot, box plot or heatmap).

The interface (see FIGS. 6A & 6C) also provides a comprehensive view where all Notes and associated information may be explored. This comprehensive view harnesses the network and relationships between Notes and the associated data and metadata to aggregate and display information based on user or system defined perspectives, e.g. chronological (date, time), organizational structure (department, study, project, experiment, chapter), genomic object (gene, biological pathway or process, drug or compound, disease or pathogen, etc.).

The System would use structured Ontologies of terms and Natural Language Processing to detect and predict categorization and additional relationships for Notes in addition to the contextual data gathered from the Note creation. Additional inferences on data relationships would be possible based on the interactions of users reviewing and collaborating upon the Notes and underlying data and metadata.

Based on Notes and underlying data relationships, or using search terms and defined areas of interest (Scientific Focus), the System would also display lists of "Related Notes" (see FIGS. 6A & 6C) to facilitate the expansion of knowledge and drawing of conclusions. By the interconnected nature of these Notes, these conclusions are recursive, as they too may be captured as an observation and/or note and semantically mined in the context of other Notes.

In addition to free form Notes, the System would include Templates to capture the Discovery Narrative, including 1) problem statement or challenge statement, 2) impact or value statements, 3) planned next steps and 3) attribution to contributing users. The System would feature an export functionality to produce reports or presentations documents including this Discovery Narrative and supporting data visualizations—gathering related Notes and underlying data and metadata.

Figure 1:
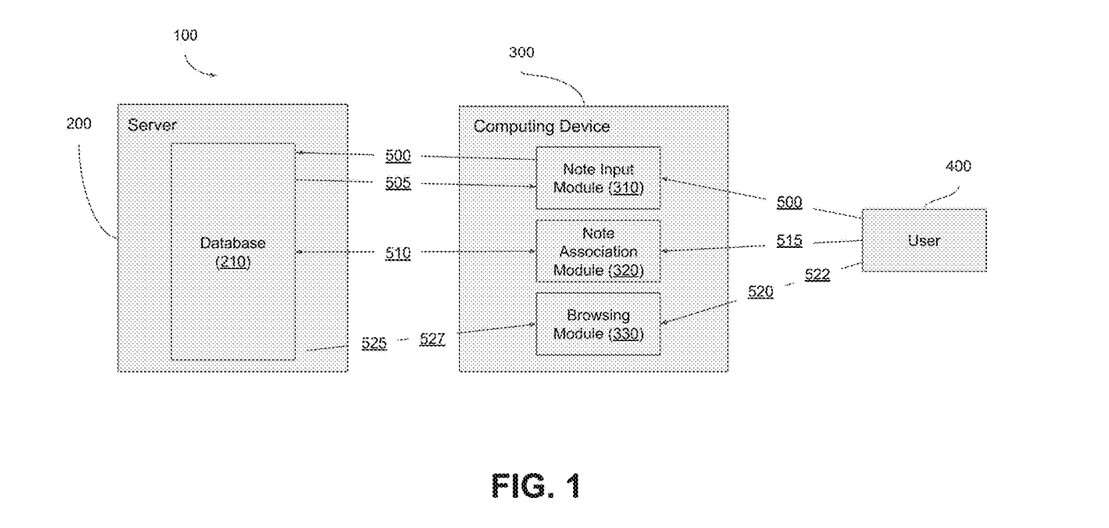
FIG. 1 shows a schematic of the system of displaying and contributing to a database of genomic information.

Referring now to FIG. 1, the present invention features a system (100) for allowing a user (400) to access and contribute to a database of genomic information (210). In some embodiments, the system (100) may comprise a server (200). In some embodiments, the server (200) may comprise the database of genomic information (210). The database of genomic information (210) may comprise a collection of derivative genomic data and a collection of metadata relating to the collection of the derivative genomic data. The system (100) may further comprise a computing device (300) communicatively coupled to the database of genomic information (210). The computing device (300) may comprise a memory storing a set of instructions and one or more processing applications, and a processor. In some embodiments, a data point of the database of genomic information (210) is selected from a group comprising a gene, a publication, an experiment, a disease, a treatment, a point of public data, and a point of private data.

In some embodiments, the memory may comprise a Note Input Module (310) for allowing the user (400) to input a note (500) into the database of genomic information (210). The note (500) may be associated with a first data point (505) of the database of genomic information (210) and connect the first data point (505) to one or more second data points of the database of genomic information (210). In some embodiments, the note (500) comprises an initial associated data point comprising the first data point (505) and a list of associated data points comprising the one or more second data points. The Note Input Module (310) may comprise instructions for accessing the first data point (505) from the database of genomic information (210) and accepting the note (500) as input from the user (400). The note (500) may be associated with the first data point (505). The Note Input Module (310) may further comprise instructions for identifying, from the note (500), the one or more second data points to be associated with the first data point (505). The Note Input Module (310) may further comprise instructions for adding the one or more second data points to the list of associated data points of the note (500).

In some embodiments, the memory may further comprise a Note Association Module (320) for adding to the list of associated data points of a pre-existing note (510). In some embodiments, the Note Association Module (320) may comprise instructions for accessing the pre-existing note (510), identifying, from the pre-existing note (510), the one or more second data points to be associated with the first data point (505), and adding the one or more new second data points (515) to the list of associated data points of the pre-existing note (510).

Figure 5A:
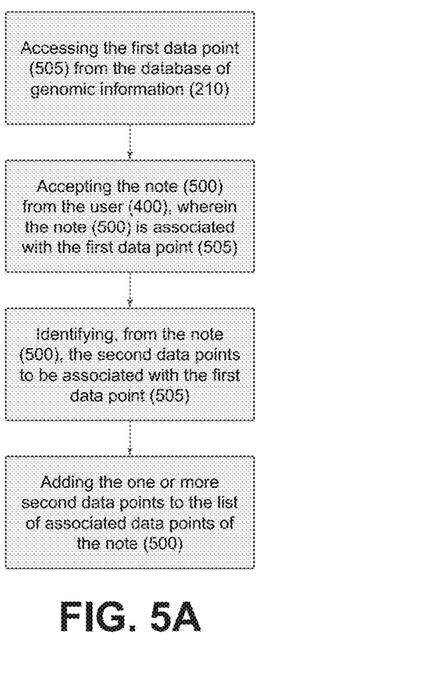
FIG. 5A shows a flow chart of a set of instructions of a Note Input Module of the present invention.
Figure 5B:
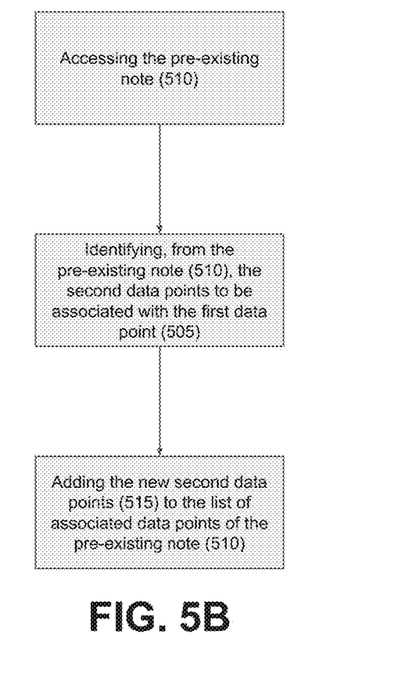
FIG. 5B shows a flow chart of a set of instructions of a Note Association Module of the present invention.
Figure 5C:
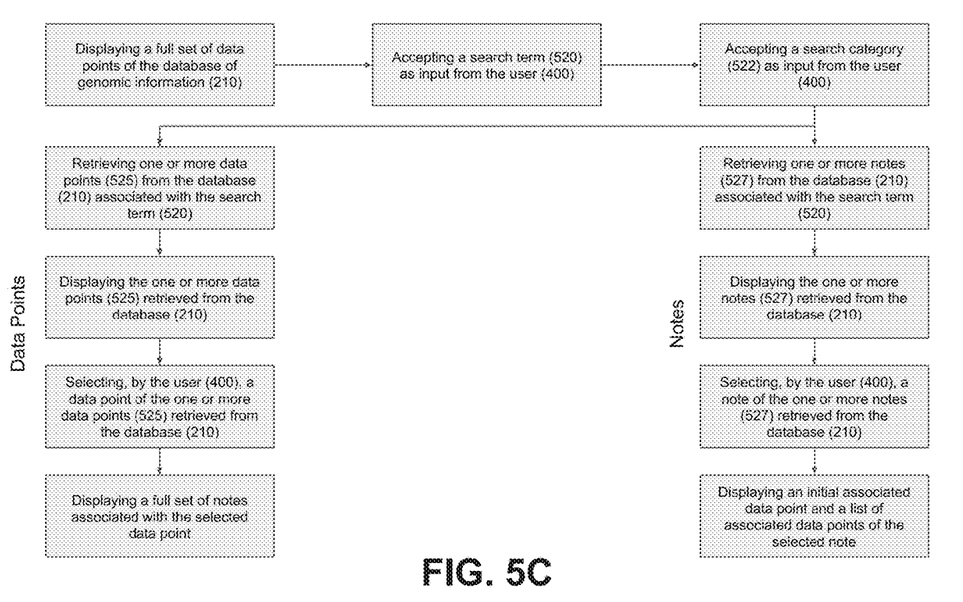
FIG. 5C shows a flow chart of a set of instructions of a Browsing Module of the present invention.

In some embodiments, the memory may further comprise a Browsing Module (330) for allowing a user (400) to search the database of genomic information (210) for data points and notes associated with the data points. In some embodiments, the Browsing Module (330) may comprise instructions for displaying a full set of data points of the database of genomic information (210). The full set of data points may be displayed in a display format. The display format may be selected from a group comprising a knowledge graph and a notebook view. The Browsing Module (330) may further comprise instructions for accepting a search term (520) as input from the user (400) and accepting a search category (522) as input from the user (400). The search category (522) may be selected from a group comprising data points and notes. If the search category (522) is data points, the Browsing Module (330) may retrieve one or more data points (525) from the database of genomic information (210) associated with the search term (520). The Browsing Module (330) may further comprise instructions for displaying the one or more data points (525) retrieved from the database of genomic information (210), and allowing the user (400) to select a data point of the one or more data points (525) retrieved from the database of genomic information (210). Upon selecting the data point, the Browsing Module (330) may display a full set of notes associated with the selected data point. If the search category (522) is notes, the Browsing Module (330) may retrieve one or more notes (527) from the database of genomic information (210) associated with the search term (520). The Browsing Module (330) may further comprise instructions for displaying the one or more notes (527) retrieved from the database of genomic information (210), and allowing the user (400) to select a note of the one or more notes (527) retrieved from the database of genomic information (210). Upon selecting the note, the Browsing Module (330) may display an initial associated data point and a list of associated data points of the selected note. In some embodiments, each note may comprise a plurality of observations, wherein each observation comprises a body of text.

In some embodiments, the process of identifying, from a note, the one or more second data points to be associated with the first data point (505), as executed by the Note Input Module (310) and the Note Association Module (320), comprises executing a natural language processing algorithm to extract terms from the note and match said terms to data points in the database of genomic information (210). In some embodiments, the process of identifying, from the note, the one or more second data points to be associated with the first data point (505) comprises accepting a user-inputted list of data points present in the database of genomic information (210). In some embodiments, the process of identifying, from the note, the one or more second data points to be associated with the first data point (505) comprises a combination of the natural language processing algorithm and the user-inputted list. In some embodiments, the process of matching terms to data points comprises identifying, based on the first data point (505), a structural relationship to another data point (i.e. a paper written as a part of a larger experiment), a time-based relationship to another data point (i.e. a data point discussed within a window of time as another data point), or a semantic relationship to another data point (i.e. terms similar to the data point). In some embodiments, matching terms to data points comprises identifying, if the first data point (505) comprises a disease or a cure, a relationship between the first data point (505) and a corresponding disease data point or cure data point. In some embodiments, matching terms to data points comprises identifying, if the first data point (505) comprises a gene, a relationship between the first data point (505) and a plurality of data points comprising a plurality of genes within a vicinity of said gene in a genome sequence.

Figure 2:
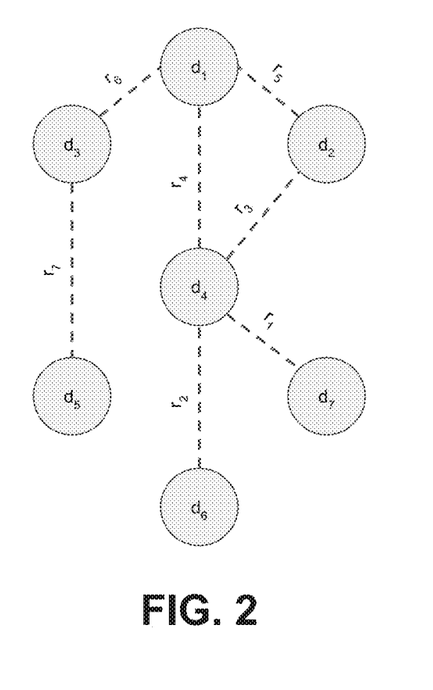
FIG. 2 shows an example of a knowledge graph display format of the Browsing Module of the system of the present invention.
Figure 3A:
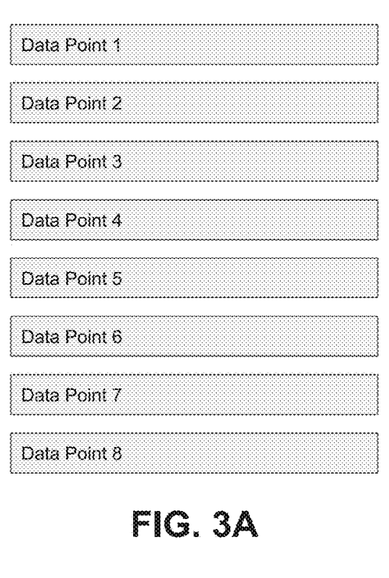
FIG. 3A shows an example of a notebook style display format of the Browsing Module of the system of the present invention in a chronological sorting style.

In some embodiments, the knowledge graph may display, for each data point of the database of genomic information (210), a definition, a value, and a set of relationships to other data points (see FIG. 2). In some embodiments, the notebook view may display the full set of data points of the database of genomic information (210) based on a sorting style selected from a group comprising chronology (see FIG. 3A), relationships between data points (see FIG. 3B), and a combination thereof. In some embodiments, the sorting style may be selected by the user (400), or identified automatically by the Browsing Module (330) based on user activity.

Figure 3B:
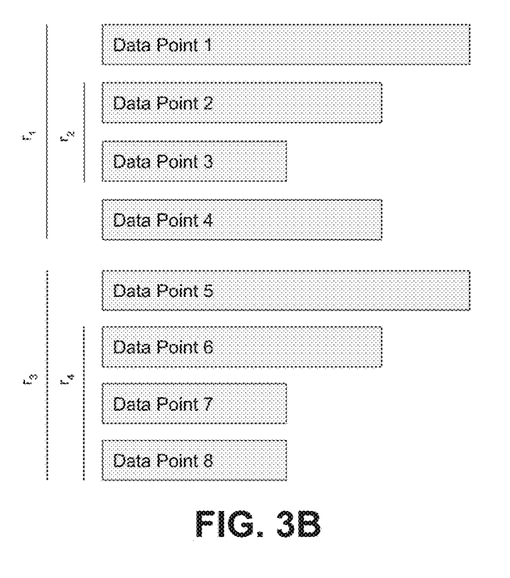
FIG. 3B shows an example of the notebook style display format of the Browsing Module of the system of the present invention in a relationship-based sorting style.

For example, if the user (400) tends to focus their browsing on the relationships between data points, the Browsing Module (330) may show the user (400) the relationships between data points while browsing.

Figure 4:
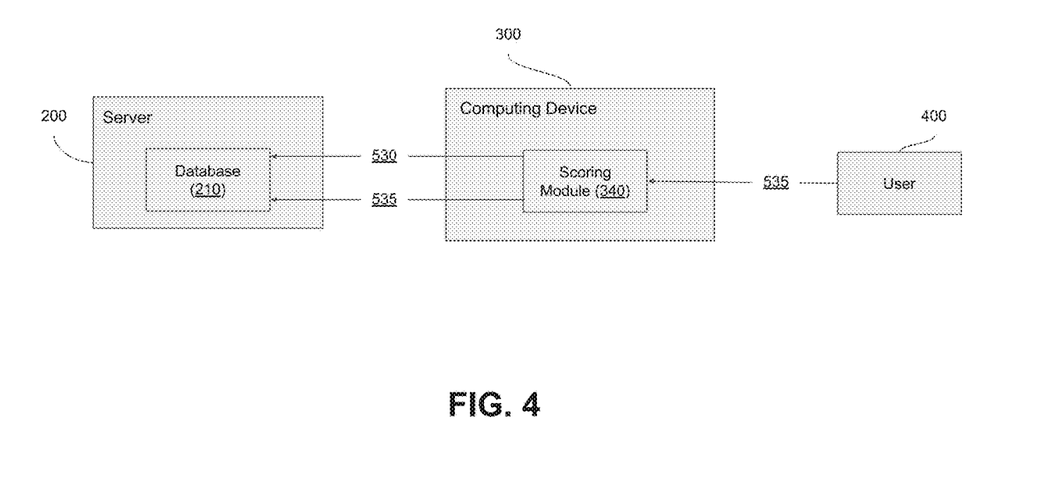
FIG. 4 shows a schematic of a Scoring Module of system of the present invention.

In some embodiments, the computing device (300) may further comprise a Scoring Module (340) for assigning a score (530) to a data point or a note. In some embodiments, the Scoring Module (340) may comprise instructions for calculating the score (530) for the data point or the note, assigning the score (530) to the data point or the note, and displaying, upon selection, the score (530) of the data point or the note. The score (530) of a data point may be calculated based on a number of supporting data points associated with the data point, and the score (530) of a note may be calculated, for each relationship between a first data point of the note and a second data point of the list of second data points of the note, based on a number of supporting data points and a number of notes associated with the relationship. In some embodiments, a supporting data point may be a data point from the database of genomic information (210) associated with the data point or the relationship. For example, a paper written on the subject of a certain genome, or a term with a semantic relationship to another term. In some embodiments, the Scoring Module (340) may further comprise instructions for accepting, from the user (400), a user score (535) for the data point or the note, assigning the user score (535) to the data point or the note, and displaying, upon selection by the Browsing Module (330), the user score (535) of the data point or the note.

In some embodiments, the Browsing Module (330) may further comprise instructions for assigning, to the user (400), a permission level, and assigning, to each data point of the database of genomic information (210) and each note of the database of genomic information (210), a permission requirement. This locks certain information from being viewed by users under a certain permission level. The Browsing Module (330) may further comprise instructions for filtering any data points from the one or more data points (525) retrieved from the database of genomic information (210) with a permission requirement that is not encompassed by the permission level of the user (400). The Browsing Module (330) may further comprise instructions for filtering any notes from the one or more notes (527) retrieved from the database of genomic information (210) with a permission requirement that is not encompassed by the permission level of the user (400). In some embodiments, the permission requirement may restrict the data point or the note from being viewed by users outside of one or more groups, outside of one or more organizations, and without a level of security clearance. In some embodiments, the permission level may be dependent on whether the user (400) is a member of the one or more groups, whether the user (400) is a member of the one or more organizations, and the level of security clearance of the user (400).

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A system (100) for allowing a user (400) to access and contribute to a database of genomic information (210), wherein the system (100) comprises:
   a. a server (200) comprising the database of genomic information (210), wherein the database of genomic information (210) comprises a collection of derivative data and a collection of metadata relating to the collection of derivative data; and
   b. a computing device (300) communicatively coupled to the database of genomic information (210) comprising a memory storing a set of instructions and one or more processing applications, and a processor, wherein the memory comprises:
      i. a Note Input Module (310) for allowing the user (400) to input a note (500) into the database of genomic information (210) wherein the note (500) is associated with a first data point (505) of the database of genomic information (210) and connects the first data point (505) to one or more second data points of the database of genomic information (210), wherein the note (500) comprises an initial associated data point comprising the first data point (505) and a list of associated data points comprising the one or more second data points, the Note Input Module (310) comprising instructions for:
         1. accessing the first data point (505) from the database of genomic information (210);
         2. accepting the note (500) as input from the user (400), wherein the note (500) is associated with the first data point (505);
         3. identifying, from the note (500), the one or more second data points to be associated with the first data point (505); and
         4. adding the one or more second data points to the list of associated data points of the note (500);
      ii. a Note Association Module (320) for adding to the list of associated data points of a pre-existing note (510), the Note Association Module (320) comprising instructions for:
         1. accessing the pre-existing note (510);
         2. identifying, from the pre-existing note (510), the one or more second data points to be associated with the first data point (505); and
         3. adding the one or more new second data points (515) to the list of associated data points of the pre-existing note (510); and
      iii. a Browsing Module (330) for allowing a user (400) to search the database of genomic information (210) for data points and notes associated with the data points, the Browsing Module (330) comprising instructions for:
         1. displaying a full set of data points of the database of genomic information (210), wherein a display format of the full set of data points is selected from a group comprising a knowledge graph and a notebook view;

2. accepting a search term (520) as input from the user (400);
3. accepting a search category (522) as input from the user (400), wherein the search category (522) is selected from a group comprising data points and notes;
4. retrieving, if the search category (522) is data points, one or more data points (525) from the database of genomic information (210) associated with the search term (520);
5. displaying the one or more data points (525) retrieved from the database of genomic information (210);
6. selecting, by the user (400), a data point of the one or more data points (525) retrieved from the database of genomic information (210);
7. displaying a full set of notes associated with the selected data point;
8. retrieving, if the search category (522) is notes, one or more notes (527) from the database of genomic information (210) associated with the search term (520);
9. displaying the one or more notes (527) retrieved from the database of genomic information (210);
10. selecting, by the user (400), a note of the one or more notes (527) retrieved from the database of genomic information (210); and
11. displaying an initial associated data point and a list of associated data points of the selected note;

wherein each note comprises a plurality of observations, wherein each observation comprises a body of text.

2. The system of claim 1, wherein identifying, from a note, the one or more second data points to be associated with the first data point (505) comprises executing a natural language processing algorithm to extract terms from the note and match said terms to data points in the database of genomic information (210), accepting a user-inputted list of data points present in the database of genomic information (210), or a combination thereof.

3. The system of claim 2, wherein matching terms to data points comprises identifying, based on the first data point (505), a structural relationship to another data point, a time-based relationship to another data point, or a semantic relationship to another data point.

4. The system of claim 3, wherein matching terms to data points comprises identifying, if the first data point (505) comprises a disease or a cure, a relationship between the first data point (505) and a corresponding disease data point or cure data point.

5. The system of claim 3, wherein matching terms to data points comprises identifying, if the first data point (505) comprises a gene, a relationship between the first data point (505) and a plurality of data points comprising a plurality of genes within a vicinity of said gene.

6. The system of claim 1, wherein the knowledge graph displays, for each data point of the database of genomic information (210), a definition, a value, and a set of relationships to other data points.

7. The system of claim 1, wherein the notebook view displays the full set of data points of the database of genomic information (210) based on a sorting style selected from a group comprising chronology, relationships between data points, and a combination thereof.

8. The system of claim 7, wherein the sorting style is selected by the user (400), or identified automatically by the Browsing Module (330) based on user activity.

9. The system of claim 1, wherein the computing device (300) further comprises a Scoring Module (340) for assigning a score (530) to a data point or a note, the Scoring Module (340) comprising instructions for:
a. calculating the score (530) for the data point or the note;
b. assigning the score (530) to the data point or the note; and
c. displaying, upon selection by the Browsing Module (330), the score (530) of the data point or the note;
wherein the score (530) of a data point is calculated based on a number of supporting data points associated with the data point;
wherein the score (530) of a note is calculated, for each relationship between a first data point of the note and a second data point of the list of second data points of the note, based on a number of supporting data points and a number of notes associated with the relationship;
wherein a supporting data point is a data point from the database of genomic information (210) associated with the data point or the relationship.

10. The system of claim 9, wherein the Scoring Module (340) further comprises instructions for:
a. accepting, from the user (400), a user score (535) for the data point or the note;
b. assigning the user score (535) to the data point or the note; and
c. displaying, upon selection by the Browsing Module (330), the user score (535) of the data point or the note.

11. The system of claim 1, wherein a data point of the database of genomic information (210) is selected from a group comprising a gene, a publication, an experiment, a disease, a treatment, a point of public data, and a point of private data.

12. The system of claim 1, wherein the Browsing Module (330) further comprises instructions for:
a. assigning, to the user (400), a permission level;
b. assigning, to each data point of the database of genomic information (210) and each note of the database of genomic information (210), a permission requirement;
c. filtering, from the one or more data points (525) retrieved from the database of genomic information (210), any data points with a permission requirement that is not encompassed by the permission level of the user (400); and
d. filtering, from the one or more notes (527) retrieved from the database of genomic information (210), any notes with a permission requirement that is not encompassed by the permission level of the user (400);
wherein the permission requirement restricts the data point or the note from being viewed by users outside of one or more groups, outside of one or more organizations, and without a level of security clearance;
wherein the permission level is dependent on whether the user (400) is a member of the one or more groups, whether the user (400) is a member of the one or more organizations, and the level of security clearance of the user (400).

* * * * *